(12) United States Patent
Adams

(10) Patent No.: US 8,622,891 B2
(45) Date of Patent: Jan. 7, 2014

(54) SEXUAL AID DEVICE

(75) Inventor: William A. Adams, St. Amant, LA (US)

(73) Assignee: Client Finance, Inc. (BZ)

( * ) Notice: Subject to any disclaimer, the term of this patent is extended or adjusted under 35 U.S.C. 154(b) by 218 days.

(21) Appl. No.: 13/187,176

(22) Filed: Jul. 20, 2011

(65) Prior Publication Data

US 2013/0023728 A1   Jan. 24, 2013

(51) Int. Cl.
*A61F 5/00* (2006.01)

(52) U.S. Cl.
USPC ........................................................... 600/38

(58) Field of Classification Search
USPC ................................ 600/38–41; 128/830–841
See application file for complete search history.

(56) References Cited

U.S. PATENT DOCUMENTS

| 4,429,689 | A | 2/1984 | Yanong |
| 5,669,869 | A | 9/1997 | Strom |
| 5,868,137 | A | 2/1999 | Brown |
| 2009/0281373 | A1 | 11/2009 | Mark |

*Primary Examiner* — John Lacyk
(74) *Attorney, Agent, or Firm* — Roy Kiesel Ford Doody & Thurmon APLC

(57) ABSTRACT

A sexual aid device to provide increased sexual sensation in either heterosexual or homosexual intercourse characterized by a structure maintaining the male penis in pressure contact with the sensitive members of the female vagina or male anus.

8 Claims, 3 Drawing Sheets

SEXUAL AID DEVICE

BACKGROUND OF THE INVENTION

1. Field of the Invention

This invention relates in general to methods and devices for increasing human sexual arousal and satisfaction. More particularly, the invention relates to methods and devices for maintaining proper positioning of the penis within a female vagina or a male anus for enhancing penile and vaginal/anal stimulation during sexual intercourse.

2. Prior Art

The prior art contains numerous devices related to sex toys and sexual aids that increase stimulation of the female or male genitalia during sexual intercourse. However, as a person ages or repeatedly engages in sexual intercourse or in the case of a female resulting from child birth there can be an expansion of the vagina or anus that makes it more difficult to maintain the physical contact between the male penis and the sexually sensitive areas of the vagina or the anus cavity.

At least with respect to heterosexual intercourse one solution proposed in the prior art is the device described in US 2009/0281373 that is structured to occupy space within an enlarged female vagina. However, such devices are cumbersome and awkward in appearance, and are designed for movement during the sexual intercourse that can result in loss of the desired positioning of the male penis within the vagina. Still further such devices are inappropriate for homosexual intercourse.

Therefore, there continues to be a need for a device that is not intrusive in appearance and can provide and maintain enhanced sexual sensitivity during either heterosexual or homosexual intercourse.

OBJECTS AND SUMMARY OF THE INVENTION

Therefore, one object of this invention is to provide a device that can be used to increase and maintain sexual sensitivity during either heterosexual or homosexual intercourse.

Another object of this invention is to provide a device that can position and maintain in position a male penis in pressured contact with the sexually sensitive structures members of the female vagina or the male anus during sexual intercourse.

A further object of this invention is to provide a device that aids in guiding the penis into the proper position in the vagina or anus for sexual intercourse.

A still further object of this invention is to provide a device that is not intrusive or distracting in appearance during it application prior to sexual intercourse.

Other objects and advantages of this invention shall become apparent from the ensuing descriptions of the invention.

Accordingly, this invention in one embodiment comprises a sexual aid device comprising an elongated, flexible body having a penis support member sized to be inserted into a vagina or an anus. The penis support member has an upper surface forming a generally U-shaped channel having a depth less than the diameter of a penis and a lower wall sized and shaped to contact and rest on the lower structures of the vagina or on the anal wall. The thickness of the walls from which the positioning member is constructed is between 0.50 and 3.00 inches. The length of the support member cavity is 4-8 inches, preferably less than about 6 inches. The support member is constructed from a pliable material, such as surgical rubber, having a surface texture capable of forming a contact with the vaginal or anal wall so that movement of the support member during intercourse is minimized. The device further comprises an external member attached to one end of the penis support member. The external member is sized and shaped to control the distance that the penis support member may be inserted into the vagina. In a preferred configuration the external member is further shaped to assist in guiding the penis into the support member channel and into contact with the desired sensitive areas of the vagina or anus. In a particularly preferred configuration the external member has side walls that flare outward from the support member side walls and downward from the support member to foam a funnel shaped path leading into the positioning member channel. This path will be progressively narrower as it progresses toward the support member side walls so as to assist in guiding the penis to the support member channel.

The foregoing has outlined rather broadly the features and technical advantages of the present invention in order that the detailed description of the invention that follows may be understood. Additional features and advantages of the invention will be described hereinafter which form the subject of the claims of the invention. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

The accompanying drawings illustrate a preferred embodiment of this invention. However, it is to be understood that this embodiment is not intended to be exhaustive, nor limiting of the invention. It is but one example of the construction of this invention.

PREFERRED EMBODIMENTS OF THE INVENTION

Without any intent to limit the scope of this invention, reference is made to the figures in describing the preferred embodiments of the invention.

Figure 1:
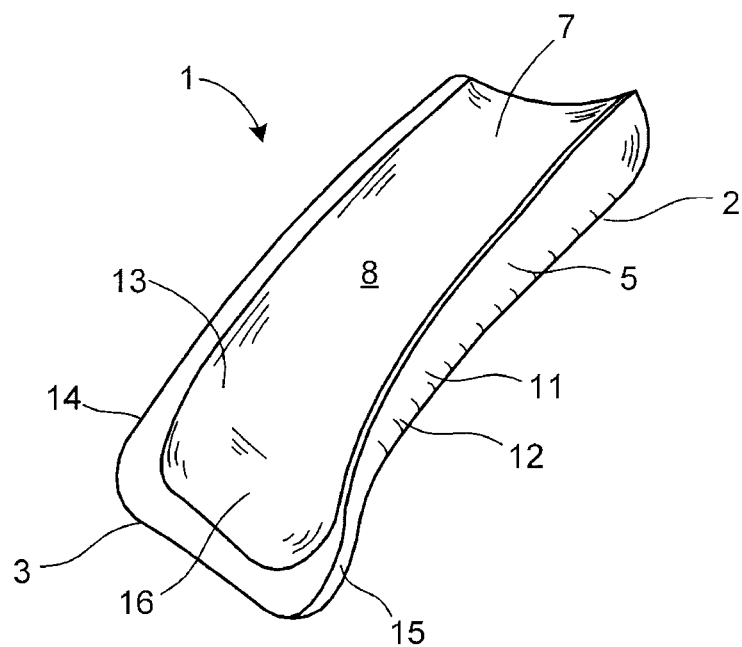
FIG. 1 is a three-quarter perspective view of a preferred embodiment of the sexual aid device of this invention.
Figure 2:
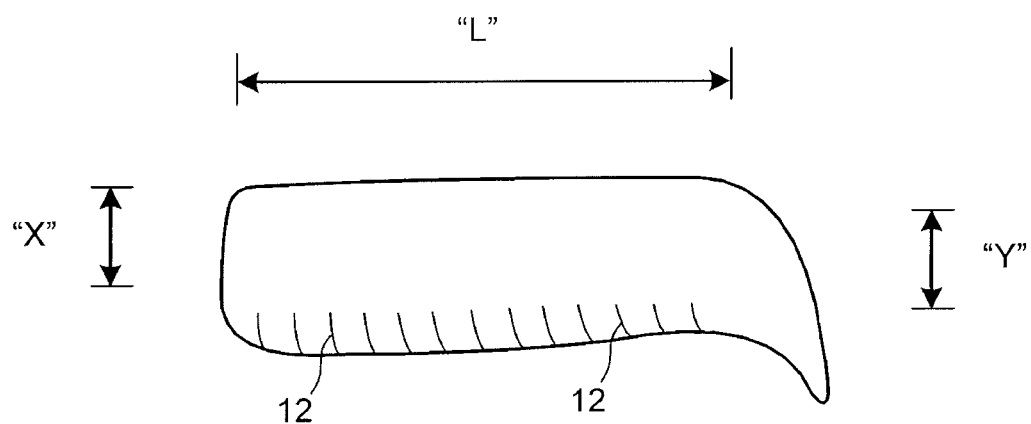
FIG. 2 is a side view of the invention illustrated in FIG. 1.
Figure 3:
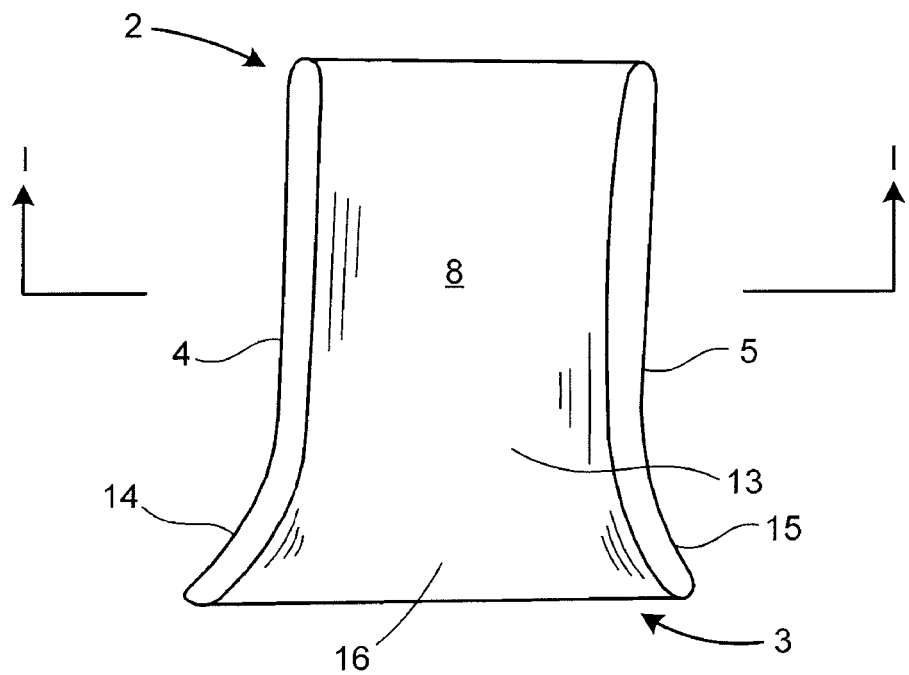
FIG. 3 is a top view of the invention illustrated in FIG. 1.
Figure 4:
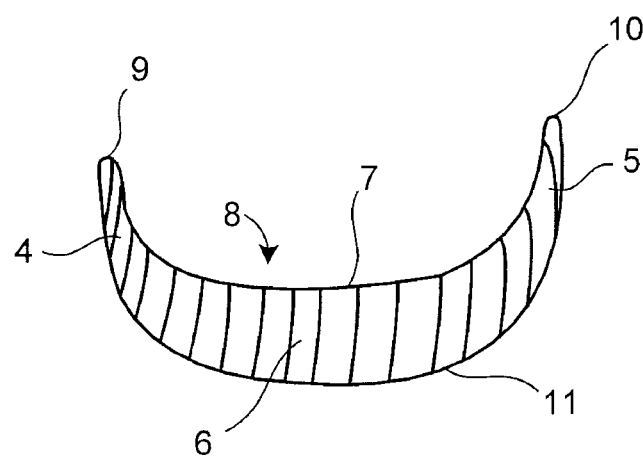
FIG. 4 is a cross-sectional view taken along lines I-I of FIG. 3.
Figure 5:
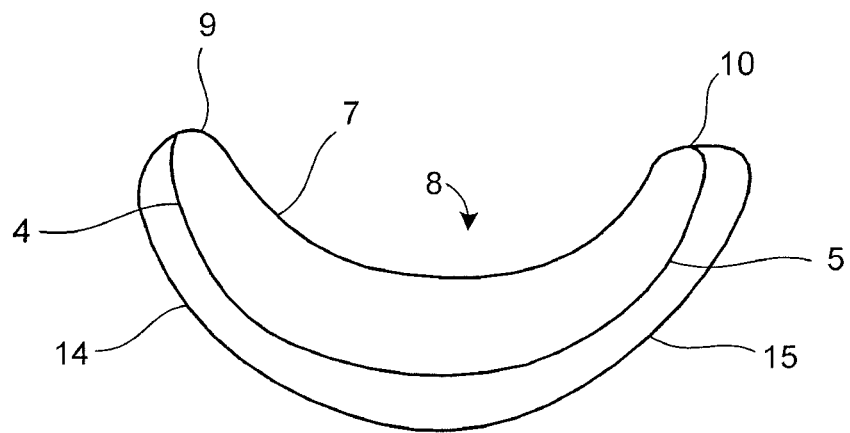
FIG. 5 is a front end view of the invention illustrated in FIG. 1.
Figure 6:
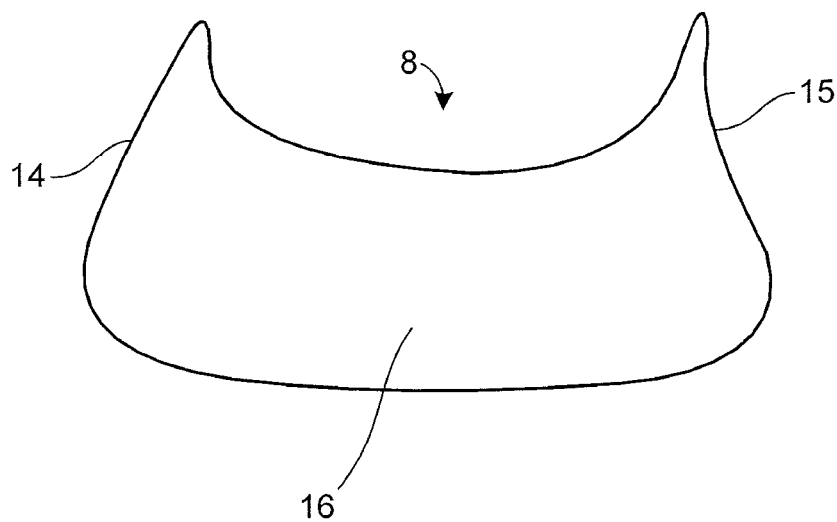
FIG. 6 is a rear end view of the invention illustrating the external member.

Referring now to the FIGS. 1-5, the sexual aid device 1 is structured to both position and support an erect penis in contact with the sexually sensitivity sections of the vagina or anus cavity. In a preferred embodiment device 1 comprises a penis support member 2 shaped to be inserted into the vagina or anus cavity and an external member 3 shaped to limit the distance that the support member 2 can be inserted and to assist in guiding the penis onto support member 2. In this preferred embodiment the penis support member 2 is elongated and preferably constructed of a pliable material, such as surgical rubber or similar soft plastic material. It is further preferred that the selected material have sufficient rigidity that it will maintain the penis is contact with the desired section of the vaginal or anal wall during sexual intercourse.

Positioning member 2 has a generally U-shaped cross-section formed by arced shaped vertical walls 4 and 5, a bottom wall 6 and a top surface 7. Top surface 7 is structured having a concave channel 8 running the length of positioning member 2. The depth "x" of channel 8 is preferably less than the diameter of an erect penis and of sufficient width that a penis can lie in channel 8 without contacting the upper lips 9 and 10 of walls 4 and 5, respectively. A channel depth of 0.25-1.00 inches is preferred. In another preferred embodiment channel 8 will extend along the entire length of penis support member 2 to better accommodate different length penis. A length "L" of 4-8 inches is preferred, and it is more preferred that the length "L" be less than 6 inches. The depth of bottom wall 6 is sufficiently deep whereby when it rests on the lower structure of the vagina or on the anus wall, it will cause the penis to contact the sexually sensitive areas of the vagina or anus wall when it is positioned in cavity 7. The depth "y" of bottom wall 6 is preferably 0.25-2.00 inches.

In a preferred embodiment the outer surface 11 of support member 2 that contacts the vagina or anus wall is constructed having a surface texture to minimize movement of device 1 during sexual intercourse once it is inserted into the vagina or anus and in contact with the vaginal or anal wall surface. It is further preferred that outer surface 11 not harm the contacted vagina or anal wall surface during sexual intercourse. Surface textures that can be employed include flexible members 12, such as, slots, trenches, ridges, raised buttons, studs, or similar structures or a combination thereof that will retard the movement of support member 2 during sexual intercourse.

The external member 3 is preferably constructed of the same material as the support member 2 to present an appearance as a continuation from end section 13 of the positioning member 2. External member 3 is constructed having side walls 14 and 15 that flare outward from side walls 4 and 5, respectively, as well as downwardly from bottom wall 6 to form a guide section 16 that directs the penis into channel 8. Guide section 16 flares downward from end section 13 a distance sufficient for a person to grasp, and preferably less than about 0.5-2.0 inches below channel 8 and less than about 2.0 inches outward from end section 13. In this preferred embodiment external member 3 performs the functions of limiting the distance that support member 2 can be inserted into the vagina or anus and assisting in guiding the penis into channel 8. It also serves as the element of device 1 that can be grasped to insert or remove device 1 from the vagina or anus.

In operation device 1 is grasped, preferably by external member 3, and positioned with its insertion end section 17 at the entrance into the vagina or anus with channel 8 facing the desired sexually sensitive surface area of the vagina or anus wall. One then pushes on member 3 to insert support member 2 into the vagina or anus. Once member 3 contacts the out side surface of the vagina or anus wall, the device 1 has been fully inserted into the vagina or anus. The penis is then positioned on guide section 16 and slid along guide section 16 and into channel 8. After sexual intercourse has been completed and the penis withdrawn, device 1 is removed by grasping member 3 and pulling device 1 out from the vagina or anus.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What I claim is:

1. A sexual aid device comprising an elongated, flexible body having:
    a. a penis support member sized to be inserted into a vagina or an anus, the penis support member comprising side walls, a bottom wall and a top wall having an upper surface forming a generally U-shaped channel having a depth less than the diameter of a penis, the bottom wall having a lower surface shaped to contact a section of an anal wall or a vaginal wall opposite a sexually sensitive section of the anus wall or vagina wall, and
    b. an external member attached at one end of the penis support member sized and shaped to control the distance that the penis support member may be inserted into the vagina, wherein the external member comprises:
        (i) side walls flaring outward from the side walls of the penis support member; and
        (ii) a bottom wall flaring outward and downward from the bottom wall of the penis support member.

2. The sexual aid device according to claim 1 wherein
    a. the bottom wall flares outward and downward a distance of less than about 2 inches below the penis support member.

3. The sexual aid device according to claim 2, wherein the bottom wall of the external member extends outward less than about 2 inches from the support member.

4. The sexual aid device according to claim 1, wherein the support member is constructed from a pliable material having a surface texture comprising one or more flexible members formed by slots, trenches, ridges, raised buttons, studs, or a combination thereof that retards the movement of support member during sexual intercourse.

5. The sexual aid device according to claim 1, wherein the penis support member having a height between 0.50 and 3.00 inches and the channel having a length between 4 and 8 inches.

6. A method of sexual intercourse comprising:
    a. inserting a sexual aid comprising:
        (i) a penis support member sized to be inserted into a vagina or an anus, the penis support member comprising side walls, a bottom wall and a top wall having an upper surface forming a generally U-shaped channel having a depth less than the diameter of a penis, the bottom wall having a lower surface shaped to contact a section of an anal wall or a vaginal wall opposite a sexually sensitive section of the anus wall or vagina wall, and (ii) an external member extending from at one end of the penis support member, the external member sized and shaped to control the distance that the penis support member may be inserted into the vagina, with the U-shaped channel of the penis support member facing a desired section of the vagina, wherein external member comprises side walls flaring outward from the side walls of the penis support member and downwardly from the bottom wall of the penis support member to form a guide section configured to assist in guiding the penis;

b. stopping the insertion when the external member contacts an outer wall surface of the vagina;

c. positioning an erect penis on an upper surface of the external member;

d. pushing the erect penis along the upper surface and into the vagina and the U-shaped channel of the penis support member to cause contact with the desired section of the vagina; and e. moving the erect penis back and forth in the U-shaped channel.

7. A sexual aid device comprising an elongated, flexible body having:

a. a penis support member sized to be inserted into a vagina or an anus, the penis support member comprising side walls, a bottom wall and a top wall having an upper surface forming a concave channel, the bottom wall having a lower surface shaped to contact a section of an anal wall or a vaginal wall opposite a sexually sensitive section of the anus wall or vagina wall, and b. an external member attached at one end of the penis support member sized and shaped to control the distance that the penis support member may be inserted into the vagina, the external member comprising:

i. side walls flaring outward from the side walls of the penis support member and downwardly from the bottom wall of the penis support member to form a guide section configured to assist in guiding a penis.

8. The sexual aid device of claim 7 wherein the channel has a depth less than the diameter of a penis.

* * * * *